United States Patent
Ramstedt et al.

(10) Patent No.: US 9,623,016 B2
(45) Date of Patent: Apr. 18, 2017

(54) ANTIBACTERIAL COMPOUNDS

(71) Applicant: Emergent Virology LLC, Gaithersburg, MD (US)

(72) Inventors: Urban Ramstedt, Bethesda, MD (US); Kelly Warfield, Adamstown, MD (US)

(73) Assignee: EMERGENT VIROLOGY LLC, Gaithersburg, MD (US)

( * ) Notice: Subject to any disclaimer, the term of this patent is extended or adjusted under 35 U.S.C. 154(b) by 0 days.

(21) Appl. No.: 14/776,111

(22) PCT Filed: Mar. 14, 2014

(86) PCT No.: PCT/US2014/028220
§ 371 (c)(1),
(2) Date: Sep. 14, 2015

(87) PCT Pub. No.: WO2014/143999
PCT Pub. Date: Sep. 18, 2014

(65) Prior Publication Data
US 2016/0000767 A1    Jan. 7, 2016

Related U.S. Application Data

(60) Provisional application No. 61/790,797, filed on Mar. 15, 2013.

(51) Int. Cl.
*A61K 31/445* (2006.01)
*A61K 31/655* (2006.01)
*A01N 43/40* (2006.01)

(52) U.S. Cl.
CPC ............ *A61K 31/445* (2013.01); *A01N 43/40* (2013.01); *A61K 31/655* (2013.01)

(58) Field of Classification Search
None
See application file for complete search history.

(56) References Cited

U.S. PATENT DOCUMENTS

| | | | |
|---|---|---|---|
| 6,225,325 | B1 | 5/2001 | Jacob |
| 2004/0097551 | A1 | 5/2004 | Butters et al. |
| 2007/0135487 | A1 | 6/2007 | Aerts |
| 2007/0275998 | A1 | 11/2007 | Butters et al. |
| 2008/0269285 | A1 | 10/2008 | Martin et al. |
| 2010/0222383 | A1* | 9/2010 | Ramstedt et al. ... A61K 31/445 514/315 |
| 2010/0317696 | A1 | 12/2010 | Ramstedt et al. |

FOREIGN PATENT DOCUMENTS

| | | |
|---|---|---|
| EP | 1 528 056 A1 | 5/2005 |
| EP | 2 145 538 A1 | 1/2010 |
| WO | WO 2009/141627 A1 | 11/2009 |
| WO | WO 2010/029313 A1 | 3/2010 |
| WO | WO 2011/028781 A1 | 3/2011 |
| WO | WO 2011/151499 A1 | 12/2011 |

OTHER PUBLICATIONS

Supplementary European Search Report for EP Application No. EP 14762952.1, Munich, Germany, mailed on Aug. 31, 2016, 10 pages.

* cited by examiner

*Primary Examiner* — Gigi Huang
(74) *Attorney, Agent, or Firm* — Sterne, Kessler, Goldstein & Fox PLLC (57) ABSTRACT

Provided are iminosugars having antibacterial properties and methods of treating and/or preventing bacterial infections with such iminosugars. The present disclosure relates to antibacterial compounds and, in particular, to iminosugars having antibacterial activity. One embodiment is a method of treating or preventing a bacterial infection comprising administering to a subject in need thereof an antibacterial effective amount of a compound of the following formula: or a pharmaceutically acceptable salt thereof.

5 Claims, 4 Drawing Sheets

Figure 1

Disk Diffusion Results – UV-4B

Figure 2

Disk Diffusion Results – UV-5

Figure 3

UV-4B and UV-5 Protective Efficacy Against *S. aureus* Challenge in Mice: Survival Data

- Mice that did not receive a control-treatment of water (n=5) all died within 24 hours of infection with a mean time-to-death (MTD) of 4 days. Mice treated with water TID displayed 30% survival and a MTD of 6 days.
- Mice treated with UV-4B or UV-5 displayed an MTD of >13 days with 80 and 70% survival, respectively.
- Significance (p<0.05) in survival is shown between the water-control group and the group dosed with UV-4B.
- Mice that were given Hog mucin (3%) on the day of infection (without bacterial challenge) displayed 100% survival (data not shown).

Figure 4

ANTIBACTERIAL COMPOUNDS

PRIORITY

The present application is the U.S. National Stage of PCT/US2014/028220 filed Mar. 14, 2014, which claims priority to U.S. provisional application No. 61/790,797 filed Mar. 15, 2013.

FIELD

The present disclosure relates to antibacterial compounds and, in particular, to iminosugars having antibacterial activity.

SUMMARY

One embodiment is a method of treating or preventing a bacterial infection comprising administering to a subject in need thereof an antibacterial effective amount of a compound of the following formula:

or a pharmaceutically acceptable salt thereof, wherein R is
a) substituted or unsubstituted oxaalkyl groups or
b) or wherein R is wherein $X_{1-5}$ are independently selected from H, $NO_2$, $N_3$, or $NH_2$;

Y is absent or is a substituted or unsubstituted $C_1$-alkyl group, other than carbonyl; and Z is selected from a bond or NH; provided that when Z is a bond, Y is absent, and provided that when Z is NH, Y is a substituted or unsubstituted $C_1$-alkyl group, other than carbonyl; and;

wherein $W_{1-4}$ are independently selected from hydrogen, substituted or unsubstituted alkyl groups, substituted or unsubstituted haloalkyl.

Another embodiment is a method of inhibiting a bacterial growth comprising contacting a bacterial population with an antibacterial effective amount of a compound of the following formula:

or a pharmaceutically acceptable salt thereof, wherein R is
a) substituted or unsubstituted oxaalkyl groups or
b) or wherein R is wherein $X_{1-5}$ are independently selected from H, $NO_2$, $N_3$, or $NH_2$;

Y is absent or is a substituted or unsubstituted $C_1$-alkyl group, other than carbonyl; and

Z is selected from a bond or NH; provided that when Z is a bond, Y is absent, and provided that when Z is NH, Y is a substituted or unsubstituted $C_1$-alkyl group, other than carbonyl; and;

wherein $W_{1-4}$ are independently selected from hydrogen, substituted or unsubstituted alkyl groups, substituted or unsubstituted haloalkyl.

Yet another embodiment is a method of killing bacteria comprising contacting a bacterial population with a bactericidal effective amount of a compound of the following formula:

or a pharmaceutically acceptable salt thereof, wherein R is
a) substituted or unsubstituted oxaalkyl groups or
b) or wherein R is wherein $X_{1-5}$ are independently selected from H, $NO_2$, $N_3$, or $NH_2$;

Y is absent or is a substituted or unsubstituted $C_1$-alkyl group, other than carbonyl; and Z is selected from a bond or NH; provided that when Z is a bond, Y is absent, and provided that when Z is NH, Y is a substituted or unsubstituted $C_1$-alkyl group, other than carbonyl; and;

wherein $W_{1-4}$ are independently selected from hydrogen, substituted or unsubstituted alkyl groups, substituted or unsubstituted haloalkyl, wherein after said contacting no growing of said bacterial population is observed.

And yet another embodiment is a method of inhibiting an alpha toxin hemolysis comprising contacting a bacterial population with an effective amount of a compound of the following formula:

or a pharmaceutically acceptable salt thereof, wherein R is
a) substituted or unsubstituted oxaalkyl groups or
b) or wherein R is wherein $X_{1-5}$ are independently selected from H, $NO_2$, $N_3$, or $NH_2$;

Y is absent or is a substituted or unsubstituted $C_1$-alkyl group, other than carbonyl; and Z is selected from a bond or NH; provided that when Z is a bond, Y is absent, and provided that when Z is NH, Y is a substituted or unsubstituted $C_1$-alkyl group, other than carbonyl; and;

wherein $W_{1-4}$ are independently selected from hydrogen, substituted or unsubstituted alkyl groups, substituted or unsubstituted haloalkyl.

DETAILED DESCRIPTION

Related Documents

The following patent documents, which are all incorporated herein by reference in their entirety, may be useful for understanding the present disclosure:

1) U.S. Pat. Nos. 6,545,021; 6,809,803; 6,689,759; 6,465,487; 5,622,972; 8,450,345; 8,426,445; 7,256,005; 7,816,560;

2) US patent application publications nos. 2007-0275998; 2011-0184019; 2013-0237567; 2010-0222384; 2013-0150405; 2011-0065754; 2011-0065753; 2011-0065752;

3) U.S. provisional applications Nos. 61/878,286 filed Sep. 16, 2013; 61/929,704 filed Jan. 21, 2014 and 61/943,918 filed Feb. 24, 2014.

DEFINITION OF TERMS

Unless otherwise specified, "a" or "an" means "one or more."

The term "antibacterial compound or agent" means a compound or agent that kills bacteria and/or inhibits the growth of bacteria.

The term "bactericidal compound or agent" means a compound or agent that kills bacteria.

The term "bacteriostatic compound or agent" means a compound or agent that inhibits and/or prevents the growth of bacteria.

The term "bacterial infection" refers to any infection caused by bacteria.

The term "treating or preventing bacterial infection" means ameliorate or alleviate the symptoms of the disease caused by the bacterial infection. The treatment is considered therapeutic if it results in at least one of the following: killing bacteria causing the infection; preventing growth of bacteria causing the infection; decreasing in mortality and/or morbidity due to the disease the disease caused by the bacterial infection.

The present inventors discovered that certain iminosugar compounds may have antibacterial properties, i.e. able to kill bacteria and/or inhibit the growth of bacteria.

In some embodiments, the iminosugar having antimicrobial properties may be an N-substituted deoxynojirimycin, such as a compound having the formula, or a pharmaceutically acceptable salt thereof, wherein R substituted or unsubstituted oxaalkyl groups; wherein $W_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups.

In some embodiments, R may be substituted or unsubstituted oxaalkyl groups comprise from 1 to 16 carbon atoms, from 4 to 12 carbon atoms or from 8 to 10 carbon atoms, which may contain from 1 to 5 or from 1 to 3 or from 1 to 2 oxygen atoms. The term "oxaalkyl" includes hydroxyterminated and methoxyterminated alkyl derivatives.

In some embodiments, R may be selected from, but is not limited to —$(CH_2)_6OCH_3$, —$(CH_2)_6OCH_2CH_3$, —$(CH_2)_6O(CH_2)_2CH_3$, —$(CH_2)_6O(CH_2)_3CH_3$, —$(CH_2)_2O(CH_2)_5CH_3$, —$(CH_2)_2O(CH_2)_6CH_3$; —$(CH_2)_2O(CH_2)_7CH_3$; —$(CH_2)_9$—OH; —$(CH_2)_9OCH_3$.

In some embodiments, R may be branched or unbranched, substituted or unsubstituted alkyl group. In certain embodiments, the alkyl group may be a long chain alkyl group, which may be C6-C20 alkyl group; C8-C16 alkyl group; or C8-C10 alkyl group. In some embodiments, R may be a long chain oxaalkyl group, i.e. a long chain alkyl group, which may contain from 1 to 5 or from 1 to 3 or from 1 to 2 oxygen atoms.

In some embodiments, R may have the following formula where $R_1$ is a substituted or unsubstituted alkyl group;

$X_{1-5}$ are independently selected from H, $NO_2$, $N_3$, or $NH_2$;

Y is absent or is a substituted or unsubstituted $C_1$-alkyl group, other than carbonyl; and Z is selected from a bond or NH; provided that when Z is a bond, Y is absent, and provided that when Z is NH, Y is a substituted or unsubstituted $C_1$-alkyl group, other than carbonyl.

In some embodiments, Z is NH and $R_1$—Y is a substituted or unsubstituted alkyl group, such as C2-C20 alkyl group or C4-C12 alkyl group or C4-C10 alkyl group.

In some embodiments, $X_1$ is $NO_2$ and $X_3$ is $N_3$. In some embodiments, each of $X_2$, $X_4$ and $X_5$ is hydrogen.

In some embodiments, the iminosugar may be a DNJ derivative disclosed, for example, in U.S. Patent application publication no. 2007/0275998, which is incorporated herein by reference.

In some embodiments, the iminosugar may be N-(9-Methoxynonyl) deoxynojirimycin or a pharmaceutically acceptable salt thereof, which may be, for example, a hydrochloric acid salt of N-(9-Methoxynonyl) deoxynojirimycin. Methods of preparing such a compound are disclosed, for example, in U.S. patent application publication no. 2010-022383.

In some embodiments, the iminosugar may be N—(N-{4'-azido-2'-nitrophenyl}-6-aminohexyl)deoxynojirimycin or a pharmaceutically acceptable salt thereof.

Methods of synthesizing deoxynojirimycin derivatives are disclosed, for example, in U.S. Pat. Nos. 5,622,972, 5,200,523, 5,043,273, 4,994,572, 4,246,345, 4,266,025, 4,405,714, and 4,806,650 and U.S. Patent application publication no. 2007/0275998, which are all incorporated herein by reference.

In some embodiments, an iminosugar, such as the ones disclosed above, may be used for treating and/or preventing a bacterial infection.

Bacterial infections include, but are not limited to, infections caused by *Bacillus cereus, Bacillus anthracis, Clostridium botulinum, Clostridium difficile, Clostridium tetani, Clostridium perfringens, Corynebacteria diphtheriae, Enterococcus (Streptococcus* D), *Listeria monocytogenes,* Pneumoccoccal infections (*Streptococcus pneumoniae*), Staphylococcal infections and Streptococcal infections; Gram Negative bacteria including *Bacteroides, Bordetella pertussis, Brucella, Campylobacter* infections, enterohaemorrhagic *Escherichia coli* (EHEC/*E. coli* 0157: H7) enteroinvasive *Escherichia coli* (EIEC), enterotoxigenic *Escherichia coli* (ETEC), *Haemophilus influenzae, Helicobacter pylori, Klebsiella pneumoniae, Legionella* spp., *Moraxella catarrhalis, Neisseria gonnorrhoeae, Neisseria meningitidis, Proteus* spp., *Pseudomonas aeruginosa, Salmonella* spp., *Shigella* spp., *Vibrio cholera* and *Yersinia*; acid fast bacteria including *Mycobacterium tuberculosis, Mycobacterium* avium-intracellulare, *Myobacterium johnei, Mycobacterium leprae*, atypical bacteria, *Chlamydia, Mycoplasma, Rickettsia, Spirochetes, Treponema pallidum, Borrelia recurrentis, Borrelia burgdorfii* and *Leptospira icterohemorrhagiae* and other miscellaneous bacteria, including *Actinomyces* and *Nocardia*

In some embodiments, the bacterial infection may be caused by *S. aureus, E. coli, P. aeruginosa P. aeruginosa, B. subtilis, Streptococcus pneumoniae* or any combination thereof.

In some embodiments, the bacterial infection may be caused by one or more strains selected from the following strains: *S. aureus* (USA300), *S. aureus* (Col), *S. aureus* (8324-5), *E. coli* (WT), *E. coli* (K12), *P. aeruginosa* 4858, *P. aeruginosa* 4961, *P. aeruginosa* 4990, *B. subtilis*, and *Streptococcus pneumoniae*. In some embodiments, the iminosugar may be useful to treat a bacterial infection which is caused by each of *S. aureus* (USA300), *S. aureus* (Col), *S. aureus* (8324-5), *E. coli* (WT), *E. coli* (K12), *P. aeruginosa* 4858, *P. aeruginosa* 4961, *P. aeruginosa* 4990, *B. subtilis*, and *Streptococcus pneumoniae*.

In some embodiments, the iminosugar may be used for inhibiting the growth of a bacterial population. Yet in some embodiments, the iminosugar may be used for killing bacteria.

In some embodiments, the iminosugar may be used for inhibiting an alpha toxin hemolysis, such as hemolysis of *Staphylococcus aureus* alpha toxin.

In some embodiments, the iminosugar may administered to a subject, which may be a mammal, such as a human being.

In some embodiments, the iminosugar may be used as a part of a composition, which further comprises a pharmaceutically acceptable carrier and/or a component useful for delivering the composition to an animal, which may be a mammal, such as a human. Numerous pharmaceutically acceptable carriers useful for delivering the compositions to a human and components useful for delivering the composition to other animals such as cattle are known in the art. Addition of such carriers and components to the composition of the invention is well within the level of ordinary skill in the art.

In some embodiments, the iminosugar may be in a form of a salt derived from an inorganic or organic acid. Pharmaceutically acceptable salts and methods for preparing salt forms are disclosed, for example, in Berge et al. (*J. Pharm. Sci.* 66:1-18, 1977). Examples of appropriate salts include but are not limited to the following salts: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate, and undecanoate.

In some embodiments, the pharmaceutical composition may consist essentially of iminosugar, which may mean that the iminosugar is the only active ingredient in the composition.

In some embodiments, the iminosugar, such as N-substituted deoxynojirimycin, may be used in a liposome composition, such as those disclosed in US publications nos. 2008/0138351, 2009/0252785 and 2010/0266678.

The amount of iminosugar administered to an animal to the methods of the invention may be an amount effective to kill the bacteria and/or inhibit growth of bacteria. The term "inhibit" as used herein may refer to the detectable reduction and/or elimination of a biological activity exhibited in the absence of the iminosugar. The term "effective amount" may refer to that amount of the iminosugar necessary to achieve the indicated effect. The term "treatment" as used herein may refer to reducing or alleviating symptoms in a subject, preventing symptoms from worsening or progressing, inhibition or elimination of the causative agent, or prevention of the infection or disorder caused by the bacteria in a subject who is free therefrom.

Actual dosage levels of active ingredients in the pharmaceutical compositions may vary so as to administer an amount of the active compound(s) that is effective to achieve the desired therapeutic response for a particular patient. In some embodiments, a dosage from 1 mg to 1000 mg given one, two or three times daily.

The selected dose level may depend on the activity of the iminosugar, the route of administration, the severity of the condition being treated, and the condition and prior medical history of the patient being treated. However, it is within the skill of the art to start doses of the compound(s) at levels lower than required to achieve the desired therapeutic effect and to gradually increase the dosage until the desired effect is achieved. If desired, the effective daily dose may be divided into multiple doses for purposes of administration, for example, two to four doses per day. It will be understood, however, that the specific dose level for any particular patient may depend on a variety of factors, including the body weight, general health, diet, time and route of administration and combination with other therapeutic agents and the severity of the condition or disease being treated. The adult human daily dosage may range from between about one microgram to about one gram, or from between about 10 mg and 100 mg, of the iminosugar per 10 kilogram body weight. In some embodiments, a total daily dose may be from 0.1 mg/kg body weight to 100 mg/kg body weight or from 1 mg/kg body weight to 60 mg/kg body weight or from 2 mg/kg body weight to 50 mg/kg body weight or from 3 mg/kg body weight to 30 mg/kg body weight. The daily dose may be administered over one or more administering events over day. For example, in some embodiments, the daily dose may be distributed over two (BID) administering events per day, three administering events per day (TID) or four administering events (QID). In certain embodiments, a single administering event dose ranging from 1 mg/kg body weight to 10 or 20 mg/kg body weight may be administered BID or TID to a human making a total daily dose from 2 mg/kg body weight to 20 mg/kg body weight or from 3 mg/kg body weight to 30 mg/kg body weight. Of course, the amount of the iminosugar which should be administered to an animal may depend upon numerous factors well understood by one of skill in the art, such as the molecular weight of the iminosugar and the route of administration. Pharmaceutical compositions that are useful in the methods of the invention may be administered systemically in oral solid formulations, ophthalmic, suppository, aerosol, topical or other similar formulations. For example, it may be in the physical form of a powder, tablet, capsule, lozenge, gel, solution, suspension, syrup, or the like. In addition to the iminosugar, such pharmaceutical compositions may contain pharmaceutically-acceptable carriers and other ingredients known to enhance and facilitate drug administration. Other possible formulations, such as nanoparticles, liposomes resealed erythrocytes, and immunologically based systems may also be used to administer the iminosugar. Such pharmaceutical compositions may be administered by a number of routes. The term "parenteral" used herein includes subcutaneous, intravenous, intraarterial, intrathecal, and injection and infusion techniques, without limitation. By way of example, the pharmaceutical compositions may be administered orally, topically, parenterally, systemically, or by a pulmonary route.

In some embodiments, the iminosugar having antibacterial properties may be dissolved or dispersed in a proper liquid carrier or mixed with such a carried. In some embodiments, the the iminosugar having antibacterial properties may be adsorbed it onto a proper powder carrier. As the case may be, emulsifiers, dispersants, suspending agents, spreaders, penetrants, wetting agents or stabilizers may be added whereby the iminosugar having antibacterial properties is made into preparations such as emulsions, water-dispersible powders, powders or tablets. The iminosugar having antibacterial properties may be used for foods, cosmetics and antibacterial preparations. Also, the iminosugar having antibacterial properties may be used in combination with other known antibacterial agents or known compounds considered to have an antibacterial activity.

As examples of the materials to which the iminosugar having antibacterial properties may be added and compounded, foods, fragrant products, fundamental cosmetics, hair cosmetics, toiletry products, bath agents, body care products, detergent/finishing agents, flavorous deodorants and drugs are given, however the present invention is not limited to these materials.

Examples of the above foods may include drinks such as a non-fruit juice drink, fruit juice-containing drink, lactic acid beverage and powdery drink, frozen sweets such as an ice cream, sherbet and ice sweet, deserts such as pudding, jelly, bavaroi and yoghurt, sweets such as a gum and candy and marine products made with boiled fish paste.

Examples of the fragrant products may include perfumes, toilet water, cologne and shower cologne.

Examples of the above fundamental cosmetics may include skin cream, cleansing cream, skin lotion, after-shave lotion, foundation, lipstick and talcum powder.

Examples of the above hair cosmetics may include shampoo agents such as a shampoo, rinse, conditioner, rinse-in-shampoo and treatment, hair dressing agents such as a pomade, hair tonic, hair liquid and hair jell, hair restorer, hair dying agent and cold wave agent.

Examples of the above toiletry products may include a toilet soap, bath soap and transparent soap.

Examples of the above bath agents may include a powdery bathing agent, solid bathing agent, solid foam bathing agent, bath oil and bubble bath.

Examples of the above detergents may include a powdery detergent for clothes, liquid detergent for clothes, softening and finishing agent, kitchen detergent, lavatory detergent, bath detergent, glass cleaner and mould-removing agent.

Examples of the above air care deodorants may include a gel-like air care deodorant, liquid air care deodorants, impregnated type air sol air care deodorant and mist type air care deodorant.

Examples of the above drugs may include a tablet, liquid drug, capsule type drug and granular drug.

Embodiments described herein are further illustrated by, though in no way limited to, the following working examples.

Example 1

Table 1 provides description of bacterial strains tested.

TABLE 1

| Strain | Strain No. | Bacterial group | Properties | Drug Resistace |
|---|---|---|---|---|
| S. aureus | 8325-4 | Gram positive cocci | Standard S. aureus | susceptible |
|  | USA300 | Gram positive cocci in cluster | Community MRSA | Methicillin resistant |
|  | Col (MRSA) | Gram positive cocci in cluster | hospital MRSA | Methicillin resistant |
| S. pneumoniae | ATCC 6301 | Gram positive cocci in chain | TBD | Wide range of drug resistance |
| B. subtilus | ATCC 6051 | Gram positive rod | TBD | susceptible |
| P. aeruginosa | 4858 | Gram negative rods | MDR | Wide range of drug resistance |
|  | 4961 | Gram negative rods | MDR | Wide range of drug resistance |
|  | 4990 | Gram negative rods | MDR | Wide range of drug resistance |
| E. coli | K12 | Gram negative rods | Standard E. coli | Susceptible |
| E. coli | In-house | Gram negative rods | Wild type | unknown |

Disc Diffusion

Different concentrations of antimicrobial discs were made by incorporation of defined amount of the compound and were stored in a refrigerator (4° C.). Plates were swabbed in three directions with test bacteria to give uniform growth with 0.5 McFarland inocula. Antimicrobial discs were applied to the plates as soon as possible, but no longer than 15 minutes after inoculation. The plates were incubated at 37° C. for 18 hours. The growth inhibition zones around the disc were measured.

Figure 1:
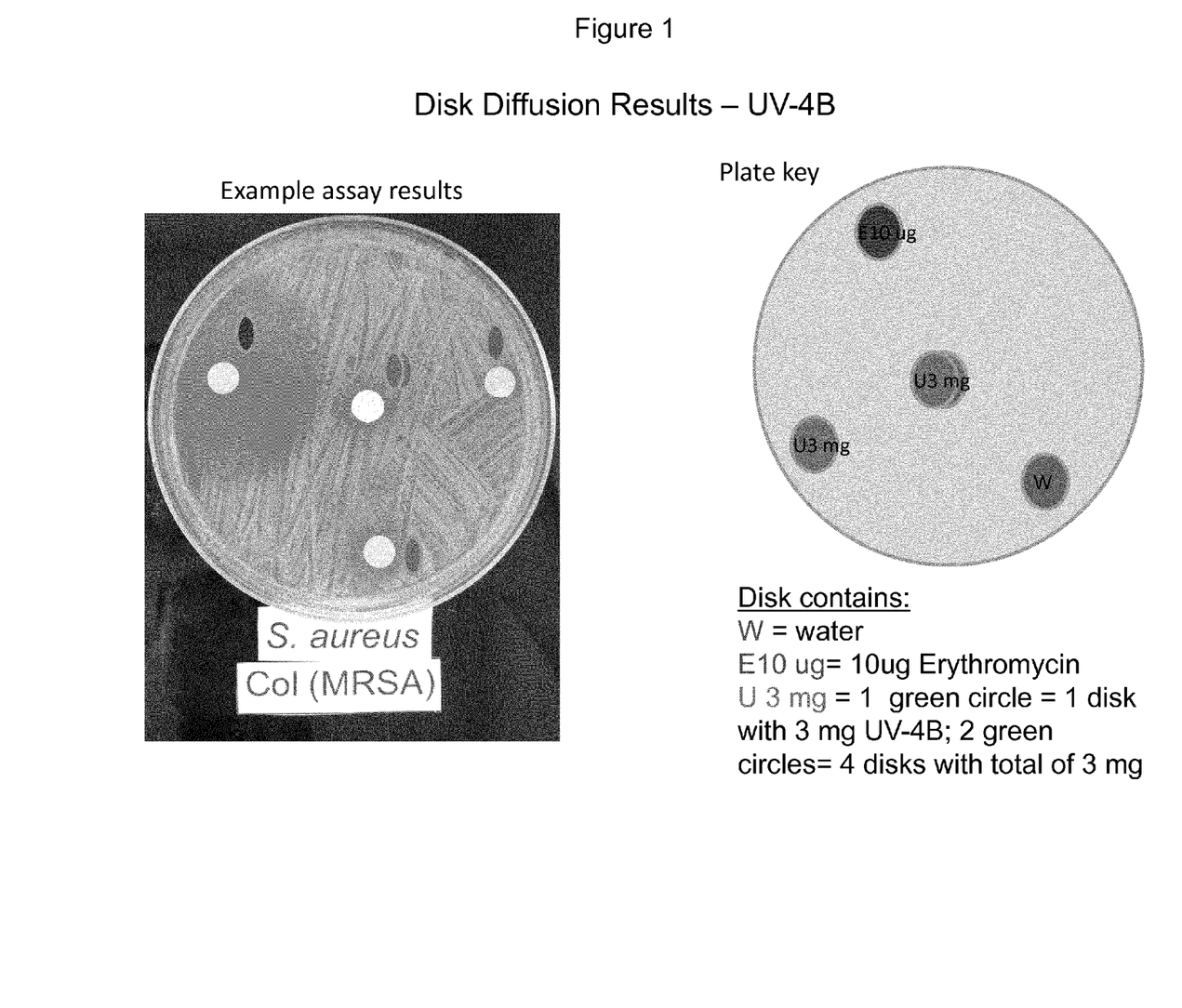
FIG. 1 relates to disk diffusion experiments for a hydrochloric acid salt of N-(9-Methoxynonyl)deoxynojirimycin (UV-4B) compound.
Figure 2:
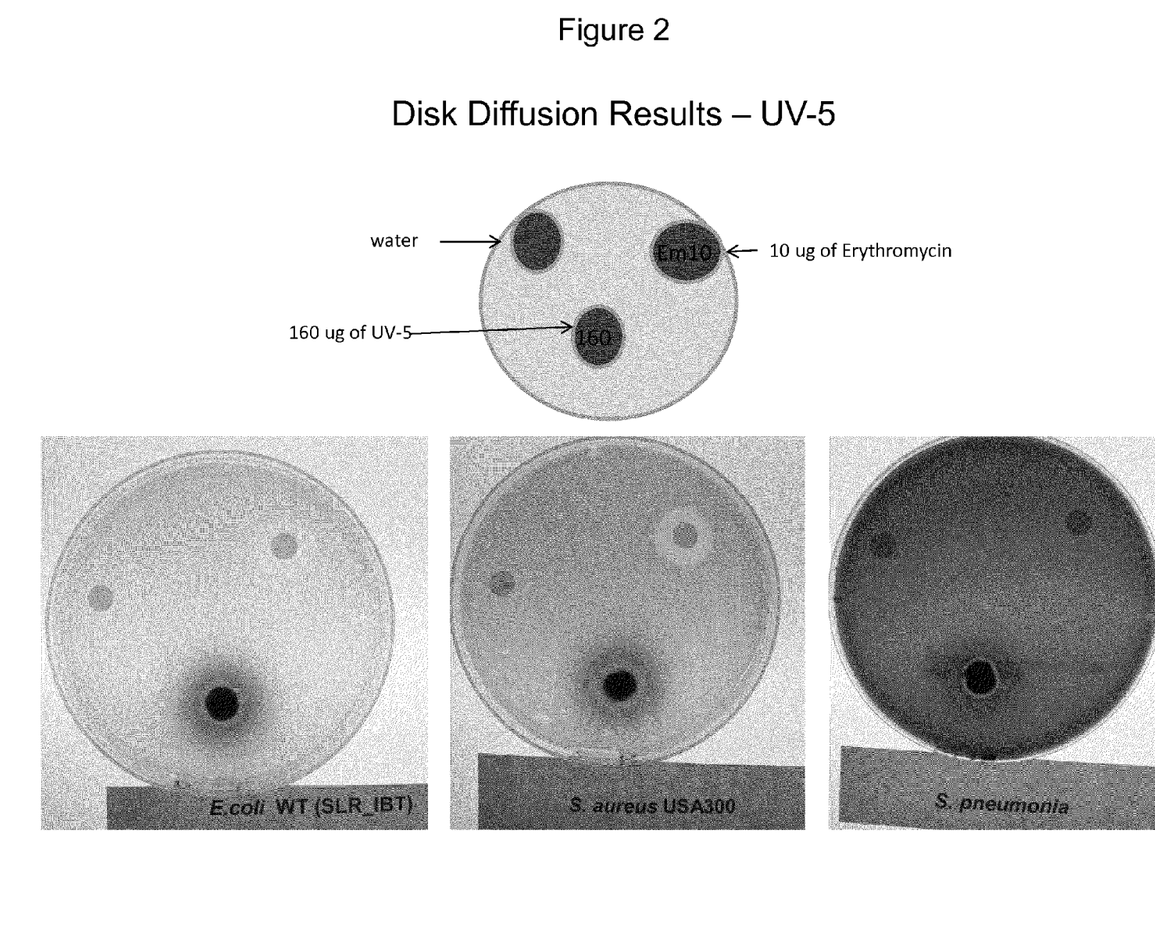
FIG. 2 relates to disk diffusion experiments for N—(N-{4'-azido-2'-nitrophenyl}-6-aminohexyl)deoxynojirimycin (UV-5) compound.

FIG. 1 presents disc diffusion results for UV-4B compound, while FIG. 2 and Table 2 summarize disc diffusion results for UV-5 compound.

TABLE 2

Disc diffusion results summary for UV-5.

| Bacteria tested | Strain No. | Inhibition zone diameter (mm) | | |
|---|---|---|---|---|
| | | UV-5 (160 ug) | Erythromycin (10 ug) | WATER |
| S. aureus | 8325-4 | 16 | 35 | 6 |
|  | USA300 | 16 | 15 | 6 |
|  | Col (MRSA) | 16 | 42 | 6 |
| S. pneumoniae | ATCC 6301 | 17 | 38 | 6 |
| B. subtilus | ATCC 6051 | 18 | 35 | 6 |
| P. aeruginosa | 4858 | 6 | 8 | 6 |
|  | 4961 | 14 | 18 | 6 |
|  | 4990 | 6 | 20 | 6 |
| E. coli | K12 | 12 | 20 | 6 |
| E. coli WT (SLR-IBT) | In-house | 15 | 15 | 6 |

Minimum Inhibitory Concentration (MIC)

The MIC assay is a technique used to determine the lowest concentration of a particular antibiotic needed to inhibit visible growth of bacteria. In this method, two fold serial dilutions of the compound were prepared in broth media. An inoculum of overnight bacterial cultures will be prepared in the same broth medium. The serial dilution tubes will be inoculated with 0.025 ml of undiluted over-night culture (1:100), a 1×10-2 dilution (1:10,000), or a 1×10-4 dilution (1:1,000,000) of bacterial suspension. Results were recorded after 24 hour incubation at 35° C. without shaking by measuring OD600. The MIC is determined by the lowest concentration of compound where no growth is visible.

Table 3 presents UV4B's MIC for various strains. Erythromycin MIC against USA300 was used as an experimental control.

TABLE 3

| Strain | UV-4B (mg/ml) | | | | | | | | | | | | MHB control | MIC (mg/ml) |
|---|---|---|---|---|---|---|---|---|---|---|---|---|---|---|
|  | 20 | 10 | 5 | 2.50 | 1.25 | 0.63 | 0.31 | 0.16 | 0.08 | 0.04 | 0.02 | 0 | | |
| S. aureus (USA300)# | − | − | − | − | + | + | + | + | + | + | ND | + | − | 2.5 |
| S. aureus (Col) | ND | − | − | − | + | + | + | + | + | + | + | + | − | 2.5 |
| S. aureus (8324-5)# | − | − | − | − | + | + | + | + | + | + | ND | + | − | 2.5 |
| E. coli (WT) | ND | − | − | + | + | + | + | + | + | + | + | + | − | 5 |
| E. coli (K12) | − | − | − | + | + | + | + | + | + | + | ND | + | − | 5 |
| P. aeruginosa 4858 | − | − | − | + | + | −* | −* | −* | −* | + | ND | + | − | 5 |
| P. aeruginosa 4961 | − | − | − | + | + | + | + | + | + | + | ND | + | − | 5 |
| P. aeruginosa 4990 | − | − | − | + | + | + | + | + | + | + | ND | + | − | 5 |
| B. subtilis | ND | − | − | − | + | + | + | + | + | + | + | + | − | 2.5 |

TABLE 3-continued

| | | | | | | | | | | | | | | | |
|---|---|---|---|---|---|---|---|---|---|---|---|---|---|---|---|
| Streptococcus pneumoniae | ND | − | + | + | + | + | + | + | + | + | ND | + | − | 10 | Based on SBA agar (not confirmatory) |

| | Erythromycin (ug/ml) | | | | | | | | | | | | |
|---|---|---|---|---|---|---|---|---|---|---|---|---|---|
| Strain | 100 | 50 | 25.00 | 12.50 | 6.25 | 3.13 | 1.56 | 0.78 | 0.39 | 0.20 | 0 | MHB control | MIC (ug/ml) |
| S. aureus (USA300) | − | − | − | − | + | + | + | + | + | + | + | − | 12.5 |

+ visible growth
− No visible growth
Two independent tests were performed
*May be experiment error Table 4 presents UV5's MIC for various strains. Erythromycin MIC against USA300 was used as an experimental control.

| | UV-4B (mg/ml) | | | | | | | | | | | | |
|---|---|---|---|---|---|---|---|---|---|---|---|---|---|
| Strain | 20 | 10 | 5 | 2.50 | 1.25 | 0.63 | 0.31 | 0.16 | 0.08 | 0.04 | 0.02 | 0 | MHB control | MIC (mg/ml) |
| S. aureus (8324-5)# | − | − | − | − | − | + | + | + | + | + | + | + | − | 1.25 |
| S. aureus (USA300)# | − | − | − | − | − | − | + | + | + | + | + | + | − | 0.0625 |
| S. aureus (Col) | − | − | − | − | − | − | + | + | + | + | + | + | − | 0.625 |
| P. aeruginosa 4858 | − | − | − | − | + | + | + | + | + | + | + | + | − | 2.5 |
| B. subtilis | − | − | − | − | − | − | + | + | + | + | + | + | − | 0.625 |

| | Erythromycin (ug/ml) | | | | | | | | | | | | |
|---|---|---|---|---|---|---|---|---|---|---|---|---|---|
| Strain | 100 | 50 | 25.00 | 12.50 | 6.25 | 3.13 | 1.56 | 0.78 | 0.39 | 0.20 | 0 | MHB control | MIC (ug/ml) |
| S. aureus (USA300) | − | − | − | + | + | + | + | + | + | + | + | − | 12.5 |

+ OD600 <0.05
− OD600 >0.05

Minimum Bactericidal Concentration (MBC)

MBC is the lowest concentration of compound required to kill an organism. For MBC determination, those cultures without visible growth from the MIC assay were re-inoculated on BHI agar plates and colony forming units (CFUs) were quantified after 24 or 48 hours of incubation at 35° C. In the case of small colony variants, growth might not occur earlier than 48 hours. A colony count with 0.1% of the original inoculum (99.9% reduction) is deemed to represent the MBC.

Table 5 presents UV4B's MBC for various strains.

TABLE 5

Minimum Bactericidal Concentration (MBC)

| | UV-4B (mg/ml) | | | | | |
|---|---|---|---|---|---|---|
| Strain | 20 | 10 | 5.00 | 2.50 | 1.25 | MBC (mg/ml) |
| S. aureus (USA300) | + | + | + | + | ND | >20 |
| S. aureus (8324-5) | − | + | + | + | ND | 20 |
| S. aureus (Col) | ND | − | − | − | + | 2.5 |
| E. coli (K12) | + | + | + | + | ND | 20 |
| E. coli (WT) | ND | − | + | + | + | 10 |
| P. aeruginosa 4858 | + | + | + | + | ND | >20 |
| P. aeruginosa 4961 | + | + | + | + | ND | >20 |
| P. aeruginosa 4990 | + | + | + | + | ND | >20 |
| B. subtilis | ND | + | + | + | + | >10 |

Table 6 presents UV5's MBC for various strains.

TABLE 6

| | UV-5 (mg/ml) | | | | | | | |
|---|---|---|---|---|---|---|---|---|
| | 20 | 10 | 5 | 2.5 | 1.25 | 0.62 | 0.3 | 0.16 | MBC (mg/ml) |
| S. Aureus NCTC8325-4 | − | − | + | + | + | + | + | + | 10 |
| S. aureus COL MRSA | − | − | −** | −** | + | + | + | + | 2.5 |
| S. aureus USA300 | − | + | + | + | + | + | + | + | 20 |

TABLE 6-continued

| | UV-5 (mg/ml) | | | | | | | | |
|---|---|---|---|---|---|---|---|---|---|
| | 20 | 10 | 5 | 2.5 | 1.25 | 0.62 | 0.3 | 0.16 | MBC (mg/ml) |
| B. subtilus | − | − | −* | −* | + | + | + | + | 2.5 |
| P. aeruginosa 4858 | − | − | − | + | + | + | + | + | 5 |

CONCLUSION

UV-4B exhibits antibacterial and bactericidal properties. UV-4B can inhibit exotoxin production suggesting a possible mechanism of action whereby virulence factor production is repressed, which could limit disease even in the presence of an ongoing infection. UV-4B may be useful in the case of antibiotic resistance.

In Vivo Efficacy of UV-4B and UV-5 in Methicillin Resistant *Staphylococcus Aureus* (MRSA) Challenge Mouse Model Study Design: This study aimed to determine the protective efficacy of UV-4B and UV-5 delivered orally to mice for 10 days (from three days before to seven days post challenge) during *Staphylococcus aureus* USA300 (USA300) infection by intraperitoneal (IP) route. The challenge inoculum included 6.13e4 cfu USA300+3% Hog mucin which causes bacteremia/sepsis within 24-72 h. A treatment regimen was based on previous toxicity and efficacy studies where 200 mg/kg of UV-4B was delivered ter in die (TID) and 100 mg/kg of UV-5 was delivered bis in die (BID) with dosing starting three days before bacterial challenge. The mice used were 6-8 week old female BALB/c mice in groups of 10. One group of 5 mice was also included to examine the potential toxicity of 3% hog mucin. Endpoint was day 10 post infection, death, or euthanasia Animals displaying severe illness as determined by >30% weight loss, extreme lethargy, or paralysis were euthanized. Observation included daily weight, health checks, and temperatures starting with the initiation of dosing until 10 days post challenge. Table 7 summarizes the study design.

TABLE 7

| Group | Treatment and Dose | Number of animals | Frequency of dosing | Challenge |
|---|---|---|---|---|
| 1 | None | 5 | N/A | 5e4 CFU of USA300 + 3% Hog Mucin |
| 2 | Vehicle | 10 | TID | |
| 3 | 200 mg/kg UV-4B | 10 | TID | |
| 4 | 100 mg/kg UV-5 | 10 | BID | |
| 5 | 200 mg/kg UV-4B | 10 | TID | 3% Hog Mucin |

Figure 3:
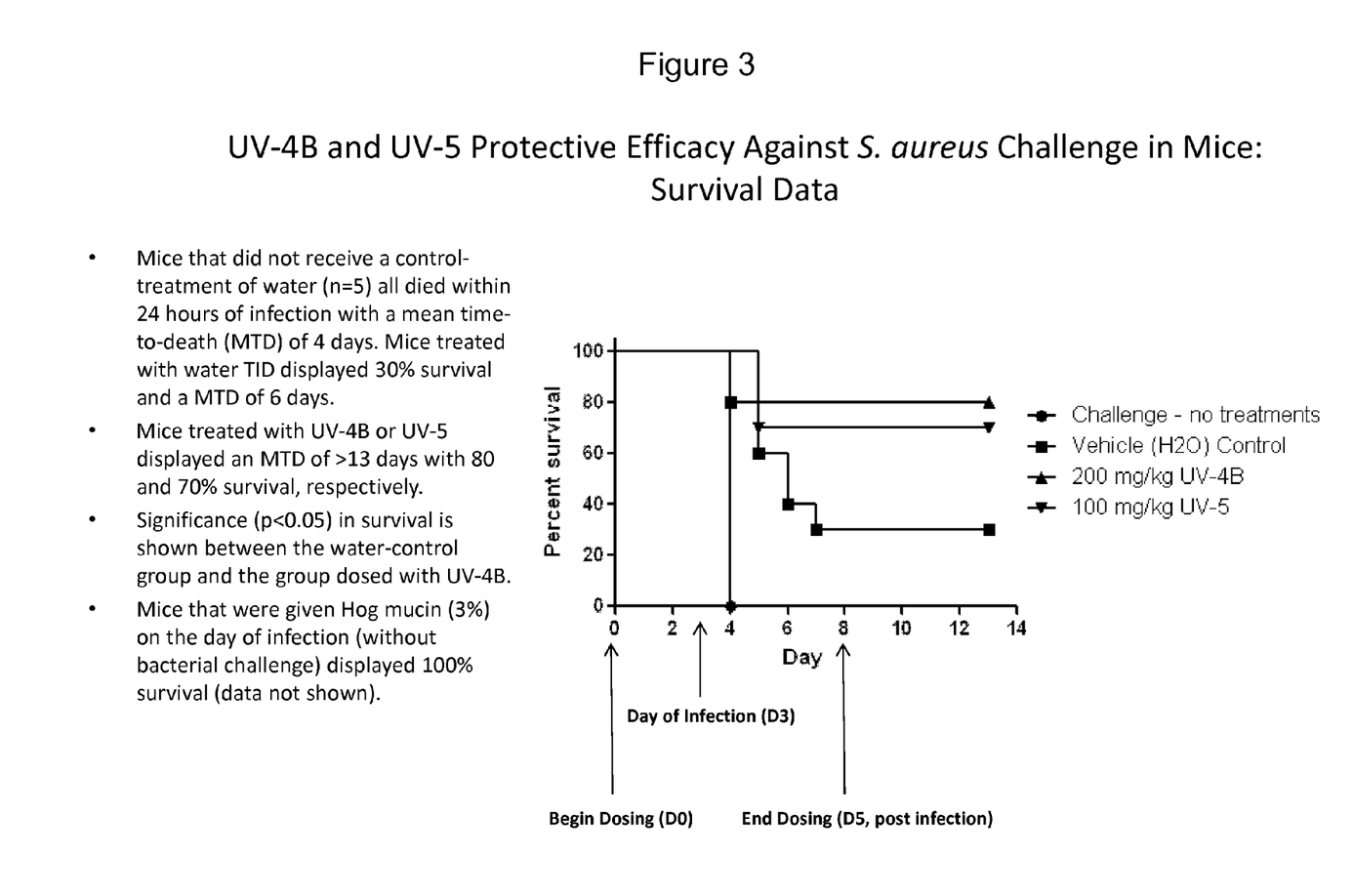
FIG. 3 presents survival data for mice challenged by *S. aureus*.

FIG. 3 presents survival data for mice challenged by *S. aureus*. Mice that did not receive a control-treatment of water (n=5) all died within 24 hours of infection with a mean time-to-death (MTD) of 4 days. Mice treated with water TID displayed 30% survival and a MTD of 6 days. Mice treated with UV-4B or UV-5 displayed an MTD of >13 days with 80 and 70% survival, respectively. Significance (p<0.05) in survival is shown between the water-control group and the group dosed with UV-4B. Mice that were given Hog mucin (3%) on the day of infection (without bacterial challenge) displayed 100% survival (data not shown in FIG. 4).

CONCLUSIONS

Mice that were infected with USA300 but did not receive any vehicle or compound treatment all died within 1 day of the IP infection. Mice that received water as the vehicle treatment had their mean time-to-death extended from 4 days (no treatment control) to 6 days, with a survival increase from 0% to 30%. The group which received 200 mg/kg of UV-4B (calculated with UV-4 free base concentration) had an increased survival rate of 80%, while the group dosed with UV-5 had a 70% survival. The mean time-to-death in the UV-4B and UV-5 treated mice was increased to >13 days post challenge. Significance is observed between the water-dosed group and the group dosed with UV-4B with a p value less than 0.05. There was not a statistically significant increase in survival between the water and UV-5 treated mice (30% and 70%, respectively); however, some toxicity was observed at the dose/regimen of UV-5 used and this may have contributed to some of the morbidity and mortality observed in this group.

Inhibition of Alpha Toxin Hemolysis

1. Grow USA300 in MHA plate O/N
2. Swab bacteria culture from plate and re-suspend in 2 ml PBS
3. Spin and discard sup.
4. Wash with 2 ml of PBS.
5. Re-suspend in 2 ml LB.
6. Make different concentration of UV-4B in LB broth.
7. Add inoculum (make two different inoculum size: 1 and 1:10 in LB). This step is very important as low inoculum may not produce any alpha toxin as it is population dependent phenomenon (see result fig: low inoculum does not produce alpha toxin)
8. Add 50 ul of inoculum in all wells but media control and UV-4b only control.
9. Read growth OD600 (T0) (see DB file at Z/: for this data).
10. Incubate at 370 C for 3 h
11. Read growth OD600 (T3).
12. Perform alpha hemolytic assay by using 2% rabbit RBC. Read OD416 nm (T3 hemolysis)

Figure 4:
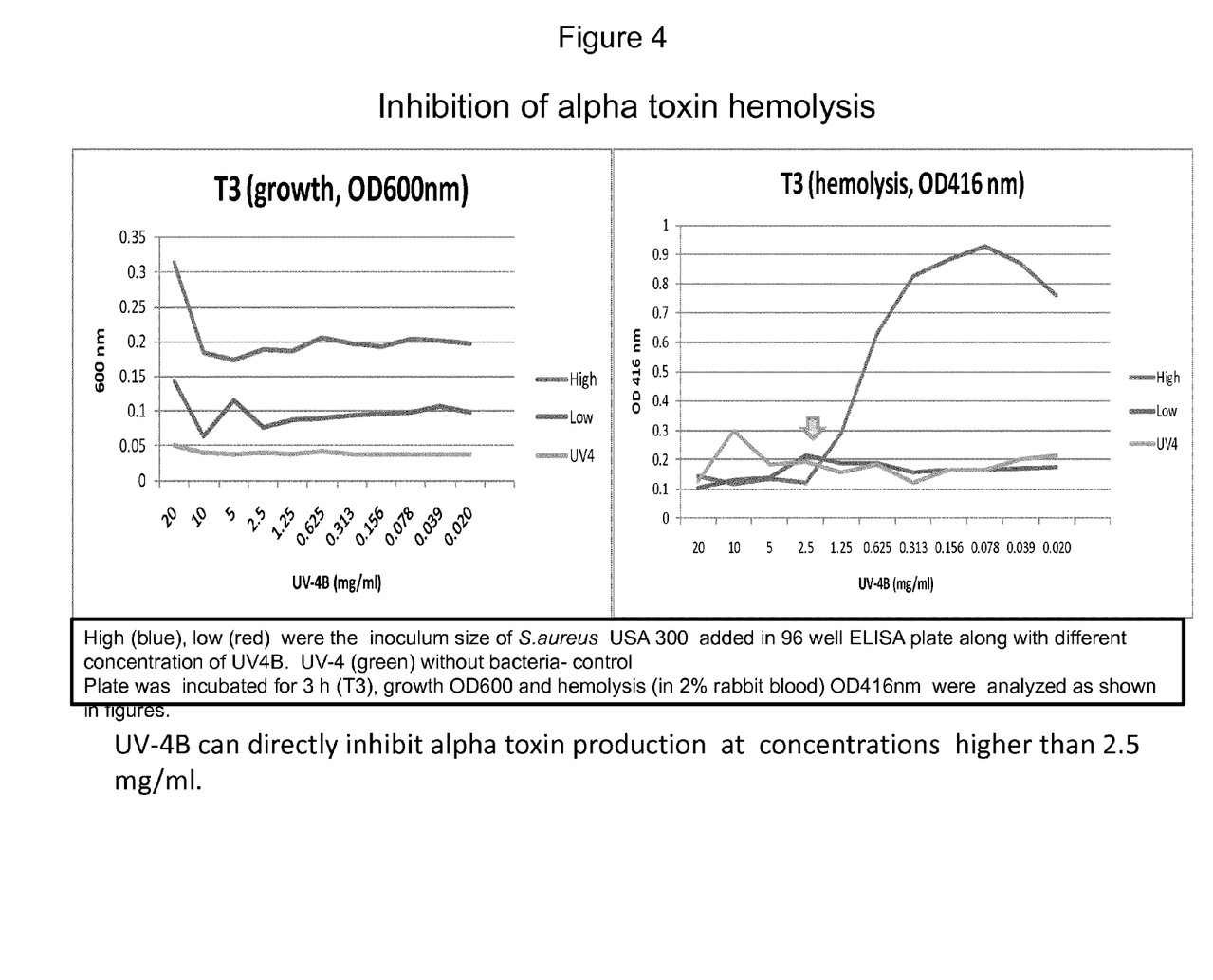
FIG. 4 presents plots of inhibition of alpha toxin hemolysis.

FIG. 4 presents data for inhibition of alpha toxin hemolysis for UV4B. High (blue), low (red) were the inoculum size of *S. aureus* USA 300 added in 96 well ELISA plate along with different concentration of UV4B. UV-4 (green) without bacteria-control. Plate was incubated for 3 h (T3), growth OD600 and hemolysis (in 2% rabbit blood) OD416 nm were analyzed as shown in FIG. 4.

Based on the data presented in FIG. 4, UV-4B may have a very important property, which may allow for inhibition of alpha toxin production at concentration higher than 2.5 mg/ml.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A method of treating or preventing a bacterial infection comprising administering to a subject in need thereof an antibacterial effective amount of a compound, which is a) N-(9-Methoxynonyl)deoxynojirimycin or a pharmaceutically acceptable salt thereof or b) N—(N-{4'-azido-2'-nitrophenyl}-6-aminohexyl)deoxynojirimycin or a pharmaceutically acceptable salt thereof, wherein said bacterial infection is caused by one or more strains selected from the group consisting of *S. aureus, E. coli, P. aeruginosa, B. subtilis,* and *Streptococcus pneumonia.*

2. The method of claim 1, wherein the subject is a human being.

3. The method of claim 1, wherein said compound is N-(9-Methoxynonyl)deoxynojirimycin or a pharmaceutically acceptable salt thereof.

4. The method of claim 3, wherein said compound is a pharmaceutically acceptable salt of N-(9-Methoxynonyl) deoxynojirimycin.

5. The method of claim 1, wherein said compound is N—(N-{4'-azido-2'-nitrophenyl}-6-aminohexyl)deoxynojirimycin or a pharmaceutically acceptable salt thereof.

* * * * *